United States Patent
Sher et al.

(10) Patent No.: US 8,397,724 B2
(45) Date of Patent: Mar. 19, 2013

(54) SYSTEM, METHOD AND VENTILATION INTERFACE FOR PROVIDING PRESSURIZED BREATHABLE GAS TO THE MOUTH AND NOSE SEPARATELY

(75) Inventors: Bruce Sher, Lighthouse Point, FL (US); Shara Hernandez, Davie, FL (US); Louis Javier Collazo, Pompano Beach, FL (US); Sanjay Chandran, Boca Raton, FL (US)

(73) Assignee: Mergent Solutions, Coconut Creet, FL (US)

( * ) Notice: Subject to any disclaimer, the term of this patent is extended or adjusted under 35 U.S.C. 154(b) by 993 days.

(21) Appl. No.: 12/341,198

(22) Filed: Dec. 22, 2008

(65) Prior Publication Data

US 2009/0159084 A1    Jun. 25, 2009

Related U.S. Application Data

(60) Provisional application No. 61/008,558, filed on Dec. 21, 2007.

(51) Int. Cl.
    *A62G 18/02* (2012.01)
(52) U.S. Cl. .......... 128/205.25; 128/205.24; 128/204.18
(58) Field of Classification Search ............. 128/204.18, 128/204.21, 204.23, 200.24, 205.25, 205.24, 128/206.11, 206.12, 206.21–206.28, 207.12
See application file for complete search history.

(56) References Cited

U.S. PATENT DOCUMENTS

| | | | | |
|---|---|---|---|---|
| 1,139,850 A | * | 5/1915 | Conkle | 128/206.28 |
| 2,336,979 A | * | 12/1943 | Boothby et al. | 128/201.19 |
| 4,926,855 A | * | 5/1990 | Hellquist et al. | 128/201.28 |
| 4,989,596 A | * | 2/1991 | Macris et al. | 128/201.28 |
| 5,243,972 A | * | 9/1993 | Huang | 128/205.25 |
| 5,560,354 A | * | 10/1996 | Berthon-Jones et al. | 128/205.25 |
| 6,123,071 A | * | 9/2000 | Berthon-Jones et al. | 128/204.18 |
| 6,394,091 B1 | * | 5/2002 | Giorgini | 128/206.21 |
| 7,007,694 B2 | * | 3/2006 | Aylsworth et al. | 128/206.11 |
| 7,658,189 B2 | * | 2/2010 | Davidson et al. | 128/205.25 |
| 7,942,148 B2 | * | 5/2011 | Davidson et al. | 128/206.11 |
| 2004/0226563 A1 | * | 11/2004 | Xu et al. | 128/206.21 |
| 2006/0196510 A1 | * | 9/2006 | McDonald et al. | 128/206.21 |
| 2008/0092898 A1 | * | 4/2008 | Schneider et al. | 128/206.28 |
| 2009/0133697 A1 | * | 5/2009 | Kwok et al. | 128/205.25 |
| 2011/0209709 A1 | * | 9/2011 | Davidson et al. | 128/205.25 |

* cited by examiner

*Primary Examiner* — Glenn Richman
(74) *Attorney, Agent, or Firm* — Maier & Maier PLLC (57) ABSTRACT

In accordance with at least one exemplary embodiment, a ventilation system for providing gas under a first pressure to the nose of a user and second pressure to the mouth of a user is disclosed. A ventilation system can include a flow generator that can be connected to a gas supply tube. The gas supply tube can be in fluid communication with a ventilation interface. At least a portion of the gas supply tube can have a divider within the channel of the tube forming a nasal passageway and an oral passageway. A nasal breathing chamber and an oral breathing chamber can be defined in the ventilation interface. The nasal breathing chamber can be in fluid communication with the nasal passageway. The oral breathing chamber can be in fluid communication with the oral passageway.

19 Claims, 5 Drawing Sheets

SYSTEM, METHOD AND VENTILATION INTERFACE FOR PROVIDING PRESSURIZED BREATHABLE GAS TO THE MOUTH AND NOSE SEPARATELY

RELATED APPLICATIONS

This application claims priority, under 35 U.S.C. §119(e), to U.S. Provisional Patent Application Ser. No. 61/008,558, filed Dec. 21, 2007, the disclosure of which is incorporated by reference herein in its entirety.

BACKGROUND

Obstructive sleep apnea syndrome (commonly referred to as obstructive sleep apnea, sleep apnea syndrome, and/or sleep apnea) is a medical condition that includes repeated, prolonged episodes of cessation of breathing during sleep. During a period of wakefulness, the muscles of the upper part of the throat passage of an individual keep the passage open, thereby permitting an adequate amount of oxygen to flow into the lungs. During sleep, the throat passage tends to narrow due to the relaxation of the muscles. In those individuals having a relatively normal-sized throat passage, the narrowed throat passage remains open enough to permit an adequate amount of oxygen to flow into the lungs. However, in those individuals having a relatively smaller-sized throat passage, the narrowed throat passage prohibits an adequate amount of oxygen from flowing into the lungs. Additionally, a nasal obstruction, such as a relatively large tongue, and/or certain shapes of the palate and/or the jaw of the individual, further prohibit an adequate amount of oxygen from flowing into the lungs.

An individual having the above-discussed conditions can stop breathing for one or more prolonged periods of time (e.g., ten seconds or more). The prolonged periods of time during which breathing is stopped, or apneas, are generally followed by sudden reflexive attempts to breathe. The reflexive attempts to breathe are generally accompanied by a change from a relatively deeper stage of sleep to a relatively lighter stage of sleep. As a result, the individual suffering from obstructive sleep apnea syndrome generally experiences fragmented sleep that is not restful. The fragmented sleep results in one or more of excessive and/or inappropriate daytime drowsiness, headache, weight gain or loss, limited attention span, memory loss, poor judgment, personality changes, lethargy, inability to maintain concentration, and depression.

Other medical conditions can also prevent individuals, including adults and infants, from receiving an adequate amount of oxygen into the lungs. For example, an infant who is born prematurely can have lungs that are not developed to an extent necessary to receive an adequate amount of oxygen. Further, prior to, during and/or subsequent to certain medical procedures and/or medical treatments, an individual can be unable to receive an adequate amount of oxygen.

Under these circumstances, it is known to use a ventilation interface to apply a positive pressure to the throat of the individual, thereby permitting an adequate amount of oxygen to flow into the lungs. In known ventilation interfaces, oxygen and/or room air containing oxygen is delivered through the mouth and/or nose of the individual.

Existing types of positive pressure applied by the known ventilation interface include continuous positive airway pressure (CPAP), in which a positive pressure is maintained in the throat passage throughout a respiratory cycle, bi-level positive airway pressure (BiPAP), in which a relatively high positive pressure is maintained during inspiration and a relatively low positive pressure is maintained during expiration, and intermittent mechanical positive pressure ventilation (IPPV), in which a positive pressure is applied when apnea is sensed (i.e., the positive airway pressure is applied intermittently or non-continuously), automatic positive airway pressure (APAP), in which a positive pressure is automatically tuned to provide the minimum required to maintain an unobstructed throat passage on a breath-by-breath basis.

Typical CPAP airflow generators can deliver air to patients at pressures between 4 and 20 cm $H_2O$. More specialized units can delivery pressures up to 25 or even 30 cm $H_2O$. Most patients typically require air delivered at pressures between 6 and 14 cm $H_2O$.

One conventional ventilation interface for the application of positive pressure includes a face mask that covers both the nose and the mouth. U.S. Pat. No. 4,263,908 (Mizerak) discloses a nasal cannula having oral gas delivery means incorporated therein adapted to increase efficiency in providing gas, such as oxygen to a patient. U.S. Pat. No. 6,123,071 (Berthon-Jones et al) discloses a combination mouth and nasal mask for assisted respiration or CPAP. At least one other exemplary ventilation interface is disclosed by U.S. Patent Application Publications Nos. 2006/0124131 (Chandran et al.) and 2006/0174887 (Chandran et al.). Other face masks include configurations that cover only the nose or only the mouth. Standard masks have air supplied under pressure and use headgear or harnesses to hold the mask on a user.

SUMMARY

According to at least one embodiment, a ventilation system can include a flow generator that can be connected to a gas supply tube having a channel. The gas supply tube can be in fluid communication with a ventilation interface. At least a portion of the gas supply tube can have a divider within the channel of the gas supply tube forming one or more nasal passageways and one or more oral passageway. One or more nasal breathing chambers and one or more oral breathing chambers can be defined in the ventilation interface. The one or more nasal breathing chambers can be in fluid communication with the one or more nasal passageways. The one or more oral breathing chambers can be in fluid communication with the one or more oral passageways. Therefore, breathable gas under a first pressure can be delivered to a wearer via the nose. Moreover, breathable gas under a second pressure can be delivered to the wearer via the mouth.

BRIEF DESCRIPTION OF THE FIGURES

Advantages of embodiments of the present invention will be apparent from the following detailed description of the exemplary embodiments thereof, which description should be considered in conjunction with the accompanying drawings in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the terms "embodiments of the invention", "embodiment" or "invention" do not require that all embodiments of the invention include the discussed feature, advantage or mode of operation.

Embodiments can be designed to cooperate with nearly any ventilation interface that makes use of a cushion for sealing engagement with portions of a user's face. For examples, embodiments can be designed to cooperate with nasal masks, oral masks, full masks and "hybrid" masks (i.e. those masks having an oral cavity and nasal prongs) of various styles and shapes, as will be readily recognized by those having ordinary skill in the art.

Embodiments described below and the principles thereof may be applied to, for example, ventilation interfaces disclosed in U.S. Patent Application Publication Nos. 2006/0124131 (Chandran et al.), 2006/0174887 (Chandran et al.), 2007/0221226 (Hansen et al.) and 2007/0272249 (Chandran et al.), the disclosures of which are incorporated by reference herein in their entireties.

Referring generally to FIGS. 1A-1D, one exemplary ventilation interface can be similar in construction to a "hybrid" ventilation mask disclosed by, for example, U.S. Patent Application Publication No. 2006/0174887. Mask 100 can have mask shell 102 with port 104 defined therein. Gas supply tube 106 can extend from mask shell 102 in fluid communication with port 104. Gas supply tube 106 can be a single piece of tubing. Alternatively, gas supply tube 106 can be more than one piece. For example, gas supply tube 106 may include various joints, including an elbow piece (not shown) extending from port 104, as one non-limiting example. Gas supply tube 106 and port 104 can be divided. Gas supply tube 106 can be divided in whole or in part.

Mask shell 102 can be coupled to cushion 108 for forming a seal around the mouth of a wearer when in use. Chin flap 110 may also be provided. Top wall 112 of cushion 108 can have apertures 114, 116 for respectively receiving nasal prongs 118, 120, which can be nasal pillows or nasal inserts. As shown, nasal prongs 118, 120 can be nasal pillows. Nasal prongs 118, 120 can be received by apertures 114, 116, respectively, so as to maintain a substantially airtight seal. Mask shell 102 can have attachment points 122 or any other type of connectors known to one having ordinary skill in the art for affixing headgear or straps (not shown) to mask 100.

Extending inside from divided port 104, the inside of mask 100 can have separated breathing chambers 124, 126 defined by divider 128. Divider 128 can thus separate the inside of mask 100 into two cavities—nasal breathing chamber 124 and oral breathing chamber 126. Divider 128 can be a one-piece or multi-piece construction. Divider 128 can extend upwards behind apertures 114, 116 proximate the bottom side of top wall 112. Alternatively, a divider (or portion thereof) can extend back far enough to be proximate the skin between the base of the nose and the upper lip of a wearer when in use. Divider 128 can be situated around the inner sides of mask shell 102 and cushion 108 so as to form a substantially airtight seal. Breathable gas can be delivered from nasal breathing chamber 124 to the nostrils of a wearer via nasal pillows 118, 120. One or more expiration holes (not shown) can be defined through mask shell 102 for each of breathing chambers 124, 126 to allow a user to exhale waste gas from each chamber 124, 126.

Divider 128 can be made of any suitable material and in any suitable shape, as will be readily appreciated by one having ordinary skill in the art. In at least one exemplary embodiment, divider 128 can be made of the same material as cushion 108. For example, divider 128 can be made of an elastomeric material, such as a silicone elastomer. As shown, divider 128 can be thicker proximate port 104. Alternatively, divider 128 may be uniformly thick or may have other portions of various thicknesses. Divider 128 can be formed integral with cushion 108 and suitably mated with the inside of mask shell 102 and port 104.

As another non-limiting example, divider 128 can be made of a rigid plastic, which can also be the same material that mask shell 102 is constructed of. Divider 128 can be integral with mask shell 102 and can be suitably mated with cushion 108. Alternatively, divider 128 can be made to be retrofitably applied to conventional masks.

In another exemplary embodiment, divider 128 can include a floor and one or more sidewalls (not shown) extending from the floor so as to form an enclosed structure around apertures 114, 116 defined in top wall 112 of cushion 108. Divider 128 can cooperate with mask shell 102 to form nasal breathing chamber 124. Divider 128 can be any of a variety of shapes.

Still referring to FIGS. 1A-1D, a flow generator (not shown) can be connected to gas supply tube 106 for delivering breathable gas to mask 100. Gas supply tube 106 can be of any suitable length. For illustrative purposes and in a non-limiting manner, gas supply tube 106 is shown truncated. The flow generator can be a CPAP machine, a BiPAP machine, an IPPV machine, an APAP machine and the like known to one having ordinary skill in the art. Gas supply tube 106 (or portions thereof) can be any flexible, thin-walled tubing known to one having ordinary skill in the art. Other portion or pieces of gas supply tube 106 may be more rigid. For example, gas supply tube 106 may include rigid plastic pieces.

At least a portion of gas supply tube 106 can include gas supply divider 130. Gas supply tube 106 can be fluidly coupled to mask 100. Gas supply divider 130 can split the gas supply tube 106 into nasal channel 132 and oral channel 134 for delivering breathable gas to nasal breathing chamber 124 and oral breathing chamber 126, respectively. Gas supply divider 130 can be planar, or, alternatively, non-planar. In at least one exemplary embodiment, gas supply divider 130 can split gas supply tube 106 into channels 132, 134 of substantially equal volume. Alternatively, gas supply divider 130 can split gas supply tube into channels 132, 134 of substantially different volumes. Accordingly, gas supply divider 130 may span the diameter of gas supply tube 106 so as to form two substantially equal cross-sectional areas. Alternatively, gas supply divider 130 may be positioned so as to form two unequal cross-sectional areas within gas supply tube 106. Gas supply divider 130 may also divide gas supply tube 106 into more than two channels in other embodiments.

Gas supply divider 130 can be constructed of the same material as gas supply tube 106 (or portions thereof). Gas supply divider 130 can be made of a flexible plastic, as one non-limiting example. Gas supply divider 130 can be equally thin-walled as gas supply tube 106 (or portions thereof) or can be thicker and thus more rigid than gas supply tube 106.

Gas supply divider 130 can be integrally formed with gas supply tube 106 (or portions thereof). Alternatively, gas supply divider 130 can be configured for insertion into gas supply tube 106 (or portions thereof). Gas supply divider 130 can be attached within gas supply tube 106 or held within gas supply tube 106 by a mating mechanism. For example, gas supply divider 130 can include a ridge portion of a tongue-in-groove mating system. Lateral groove sections can thus be defined within gas supply tube 106 for receiving the ridge portion.

Still referring to FIGS. 1A-1D, breathable gas can be communicated through nasal channel 132 and oral channel 134 at different pressures. Moreover, pressurized breathable gas from nasal channel 132 and oral channel 134 can be directed to nasal breathing chamber 124 and oral breathing chamber 126, respectively. Accordingly, the pressurized breathable gas provided to nasal breathing chamber 124 can be under a different pressure than the pressurized breathable gas provided to oral breathing chamber 126.

To provide breathable gas at different pressures to nasal breathing chamber 124 and oral breathing chamber 126, respectively, one or more valves or like mechanisms can be situated within or at any divided portion of port 104 or gas supply tube 106. The one or more valves can be set to partially obstruct channels 132, 134 within gas supply tube 106 or at port 104. The one or more valves can be any valve known to one of ordinary skill in the art. Accordingly, one or more valves can regulate the flow of pressurized breathable gas through channels 132, 134. Alternatively, singularly or in conjunction, one or more valves can regulate the flow of pressurized breathable gas entering breathing chambers 124, 126. Valves can have positions ranging from fully opened to fully closed and any selectable position there between.

Other mechanisms for controlling gas flow and/or pressure through channels 132, 134 can include providing walls having one or more openings, which may be fixed or adjustable. In other embodiments, walls having different gas permeabilities can be positioned within channels 132, 134. In further embodiments, any other methods or mechanisms for controlling gas flow and/or gas pressure known to those having ordinary skill in the art can be used. For example, nasal channel 132 and oral channel 134 can have different cross-sectional areas, which in itself can be used to regulate gas flow and/or pressure. Additionally, an external approach to changing the cross-sectional areas of channels 132, 134 can be applied, such as various clamps known to one having ordinary skill in the art. Valves and like mechanism for controlling gas flow and/or pressure may be used in combination.

Separate channels 132, 134 under the control of one or more valves or like mechanisms can allow a doctor to prescribe different pressures or ranges of pressures of breathable gas to be received nasally and orally by a patient. The patient or doctor can adjust the pressure of the breathable gas coming to the patient's nose or mouth by selecting or adjusting the corresponding valve. This may allow the doctor and patient to form a consensus on an effective treatment that may be comfortable to the patient. For example, a doctor prescribing pressurized gas or a patient prescribed pressurized gas can adjust the nasal flow to 8 cm $H_2O$ and the oral flow to 2 cm $H_2O$. Likewise, the doctor or patient can adjust the nasal flow to 4 cm $H_2O$ and the oral flow to 6 cm $H_2O$ and so on.

Figure 1A:
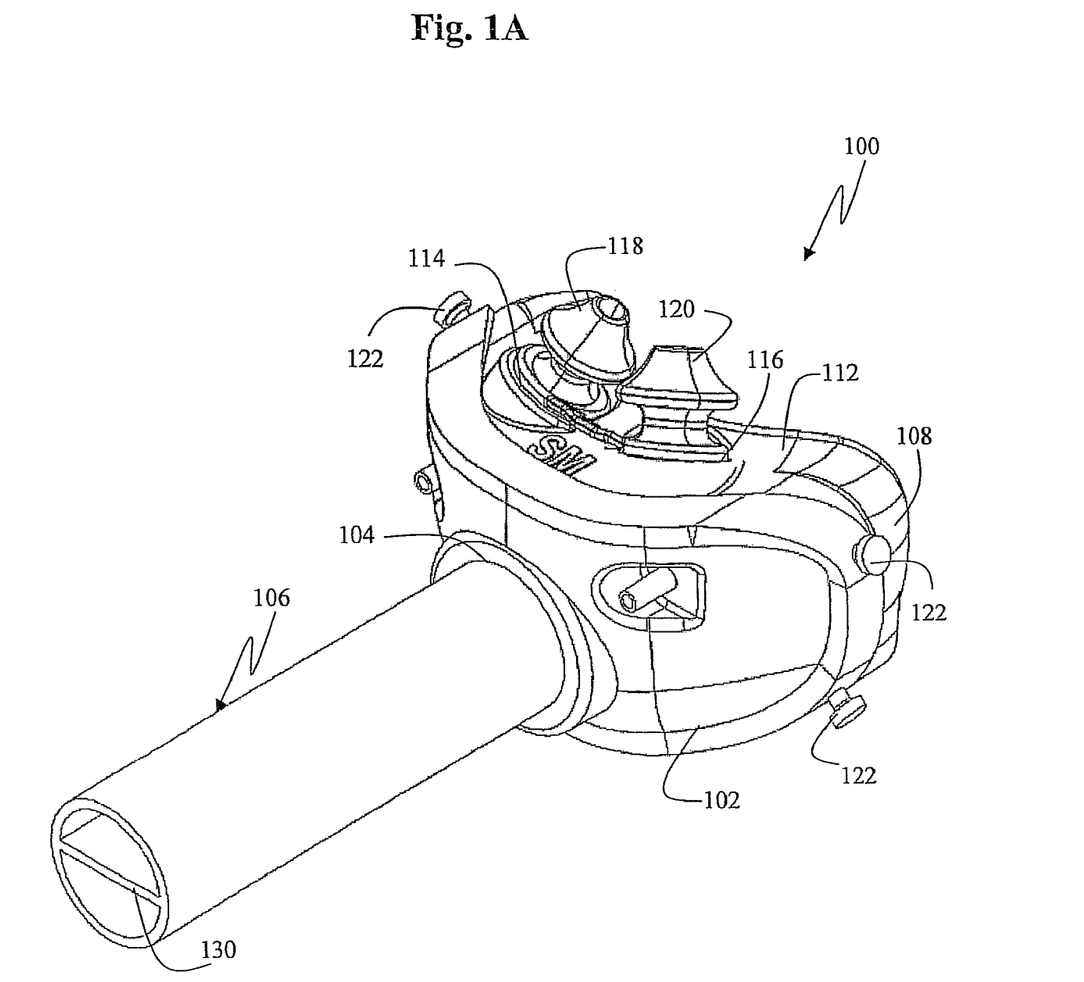
FIG. 1A is a perspective view of an exemplary "hybrid" mask and an exemplary supply tube connected thereto.
Figure 1B:
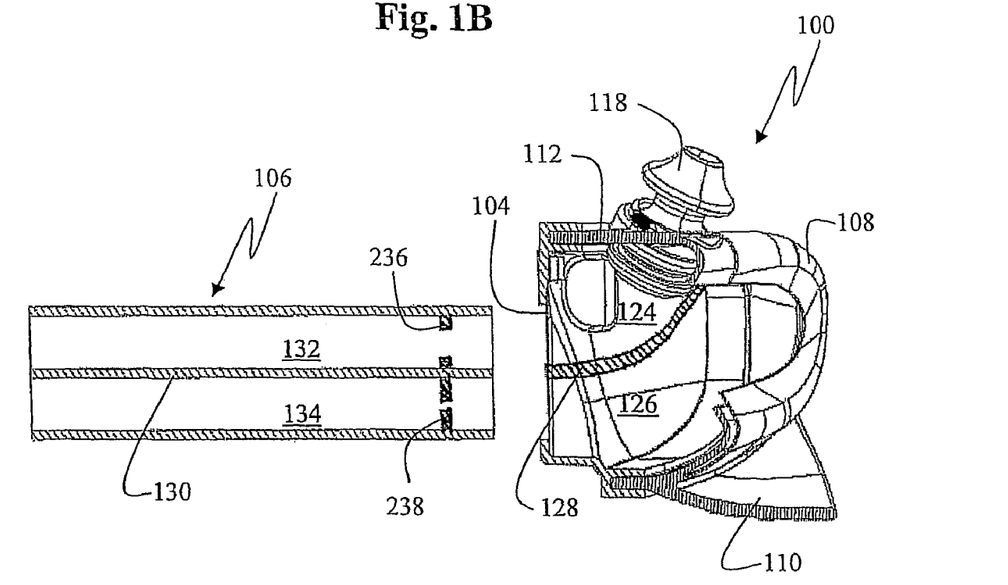
FIG. 1B is a cross-sectional view of the exemplary "hybrid" mask and the exemplary supply tube of FIG. 1A illustrating a pair of exemplary valves.

Referring particularly to FIG. 1B, first valve 236 can be disposed within any portion of nasal channel 132. Second valve 238 can be disposed within any portion of oral channel 134. As shown, first valve 236 can be set to a greater dilation than second valve 238. The greater the dilation of valves 236, 238, the greater the pressure of the breathable gas provided to chambers 124, 126, respectively.

Figure 1C:
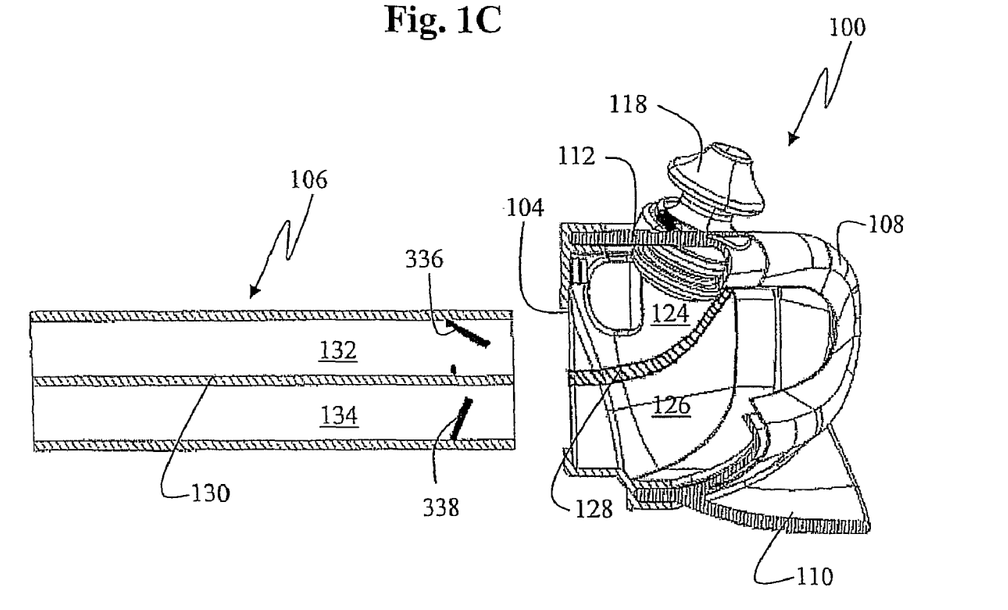
FIG. 1C is a cross-sectional view of the exemplary "hybrid" mask and the exemplary supply tube of FIG. 1A illustrating another pair of exemplary valves.

Referring particularly to FIG. 1C, first valve 336 can be disposed within any portion of nasal channel 132 and second valve 338 can be disposed within any portion of oral channel 134. As shown, first valve 336 can be set to provide less obstruction to nasal channel 132 than second valve 338 is set to provide to oral channel 134. The less obstructed channels 132, 134 are by valves 336, 338, respectively, the greater the pressure of the breathable gas that passes through the passageways of valves 336, 338.

Figure 1D:
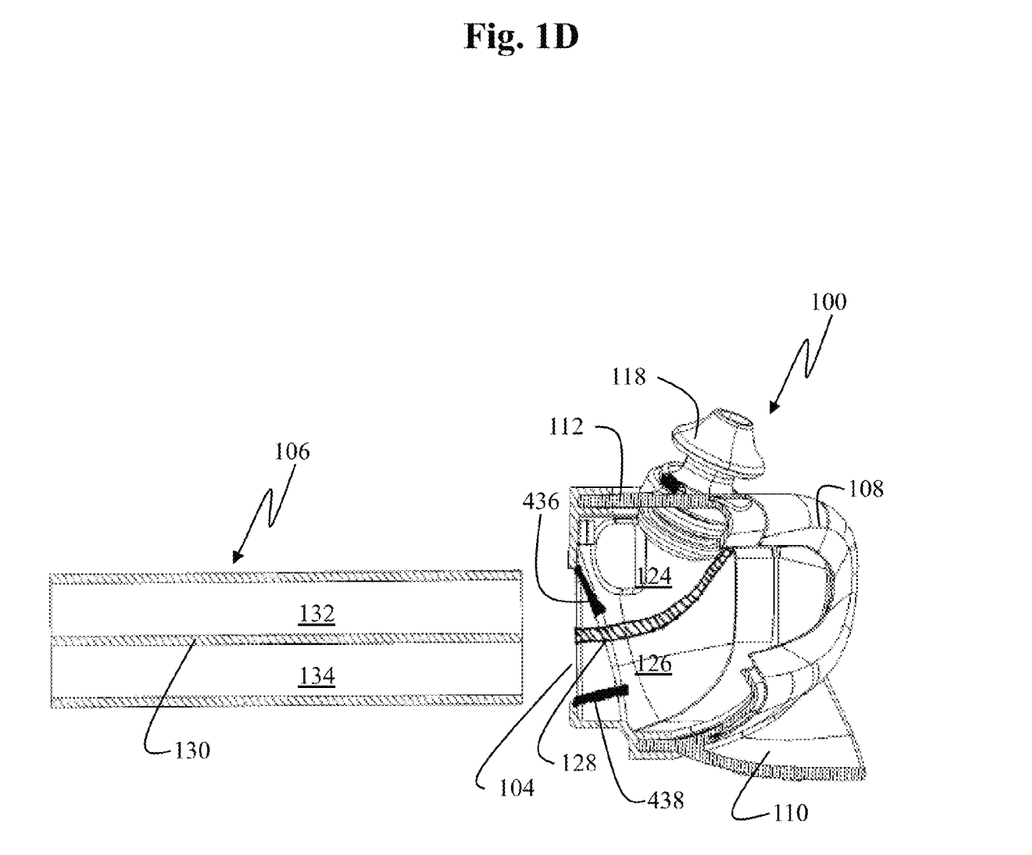
FIG. 1D is a cross-sectional view of the exemplary "hybrid" mask and the exemplary supply tube of FIG. 1A illustrating yet another pair of exemplary valves.

Referring particularly to FIG. 1D, first valve 436 can be disposed proximate the upper portion of divided port 104. Second valve 438 can be disposed proximate the lower portion of divided port 104. As shown, first valve 436 can be set to provide more obstruction to the entryway of nasal breathing chamber 124 than second valve 438 is set to provide to the entryway of oral breathing chamber 126. The greater the obstruction at the entryways of breathing chambers 124, 126, the lesser the pressure of breathable air in breathing chambers 124, 126.

In at least one other exemplary embodiment, a valve feature or like mechanism for providing breathable gas under different pressures to nasal channel 132 and oral channel 134 can be part of a CPAP unit configured to interface with divided gas supply tube 106. In other embodiments, a divided Y connector can be coupled to gas supply tube where each tube extending from an arm of the Y connector leads to a separate CPAP unit for providing breathable gas under pressure to each channel 132, 134.

In a further exemplary embodiment, mask 100 can include a divided port 104 having at least two openings that may be in fluid communication with at least two gas supply tubes 106. Each of the gas supply tubes 106 may be in fluid communication with a single breathable gas supplying device or each supply tube 106 can be connected to a different gas supplying device. Each of the gas supply tubes 106 can deliver gas at the same pressures or alternatively, the gas supply tubes 106 may also deliver gas at different pressures. Gas supply tubes 106 may each have the same cross-sectional area or they can have different cross-sectional areas. The gas supply tubes 106 may also include valves or other desired pressure or flow regulating mechanisms known to one skilled in the art.

In another exemplary embodiment, each channel 132 and 134 may include at least one divider 130, which can serve to form a plurality of different channels. Each of the plurality of channels 132 and 134 may be in fluid communication with a single breathable gas supplying device or each channel 132 and 134 can be connected to a different gas supplying device. Each of the channels 132 and 134 can deliver gas at the same pressures or alternatively, the channels 132 and 134 may also deliver gas at different pressures. Channels 132 and 134 may each have the same cross-sectional area or they can have different cross-sectional areas. Additionally, channels 132 and 134 may also include valves or other desired pressure or flow regulating mechanisms known to one skilled in the art.

Figure 2A:
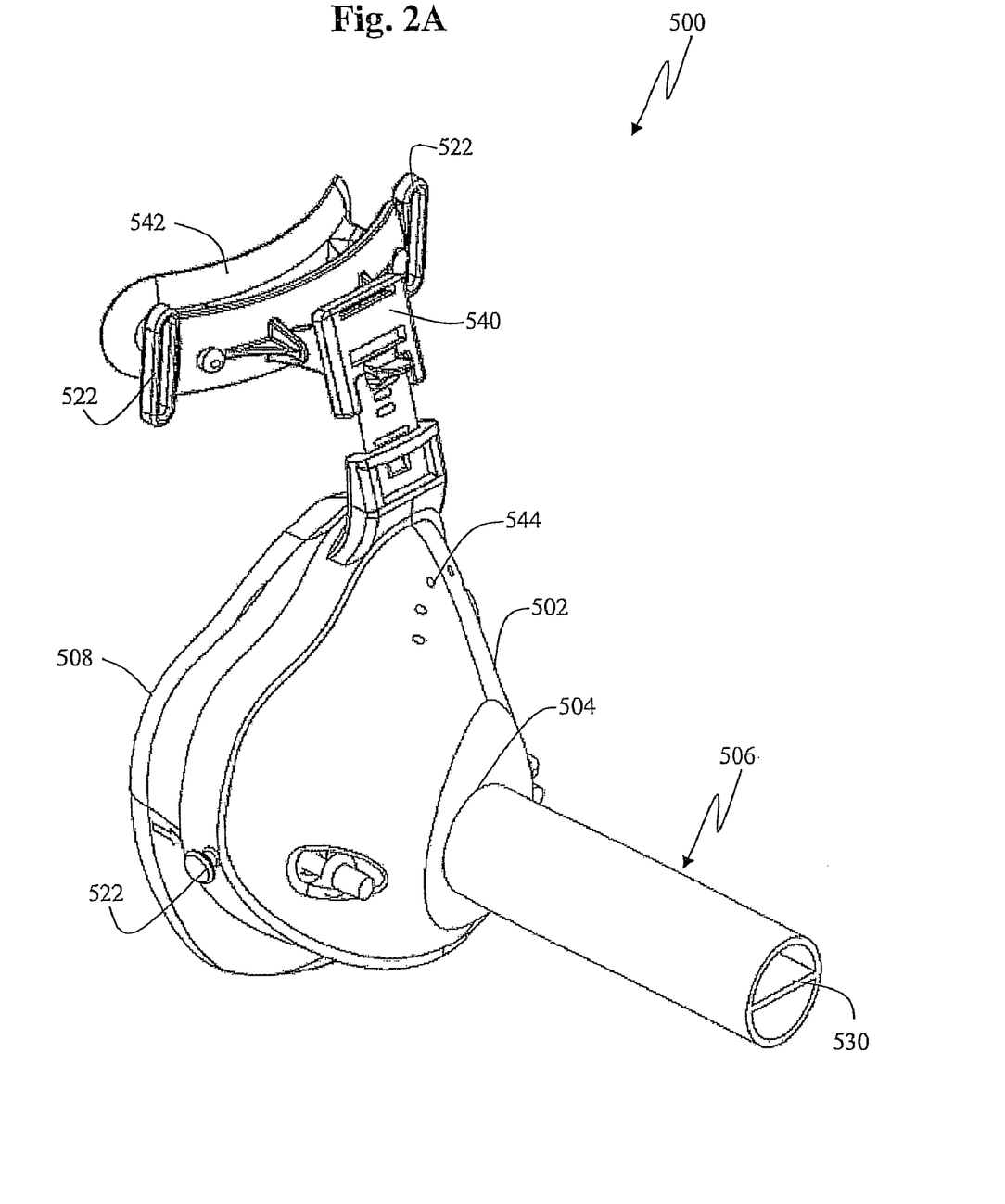
FIG. 2A is a perspective view of an exemplary full mask and an exemplary supply tube connected thereto.
Figure 2B:
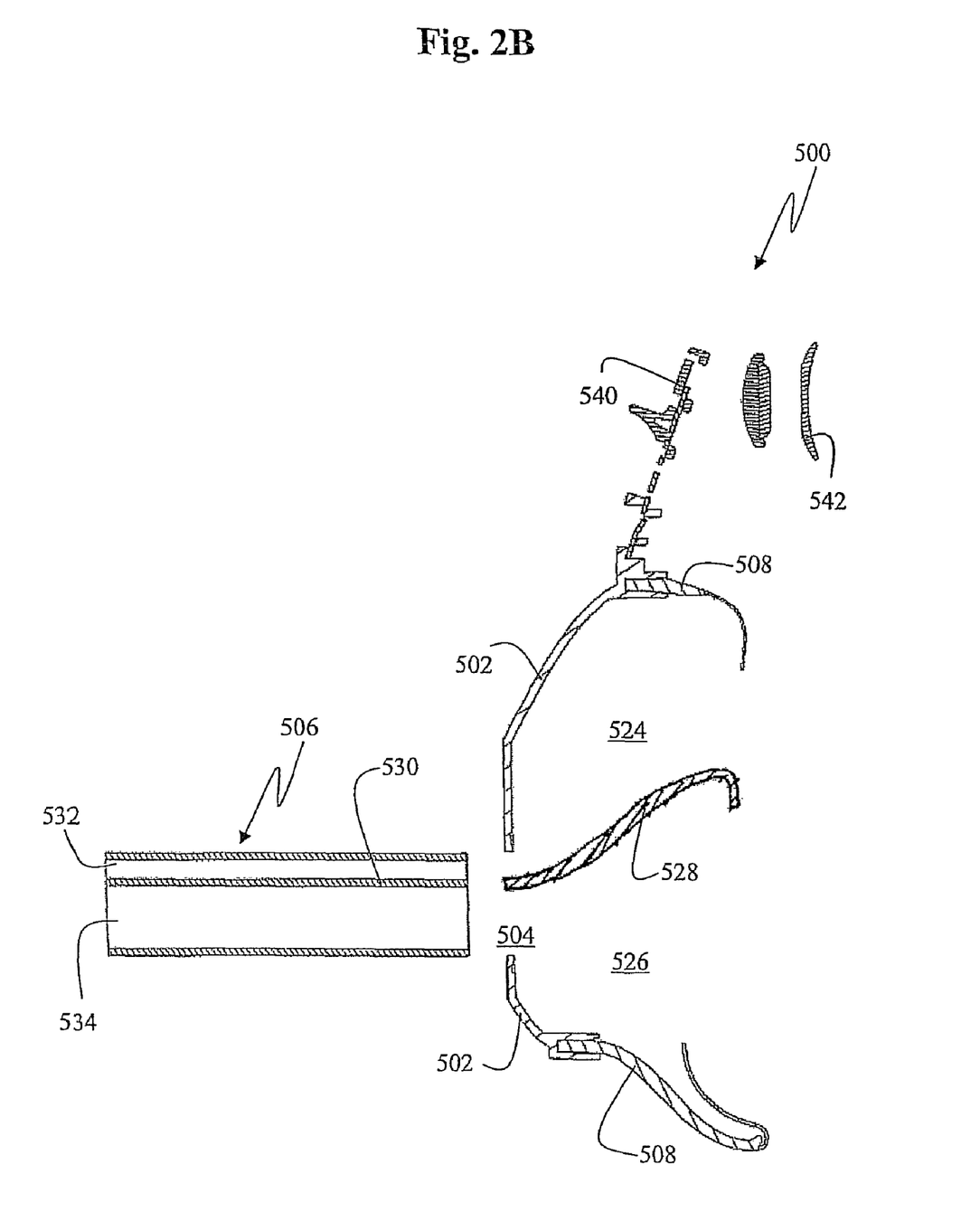
FIG. 2B schematically depicts a cross-sectional view of the exemplary full mask and the exemplary supply tube of FIG. 2A where the exemplary supply tube is detached.

Referring to FIGS. 2A and 2B, another exemplary ventilation interface in accordance with at least one other exemplary embodiment can be similar in construction to the full mask disclosed, for example, by U.S. Patent Application Publication No. 2007/0221226 (incorporated by reference above). Full mask 500 can have mask shell 502 with port 504 defined therein. Gas supply tube 506 can be a single piece of tubing. Alternatively, gas supply tube 506 can be more than one piece. For example, gas supply tube 506 may include various joints, including an elbow piece (not shown) extending from port 504, as one non-limiting example. Gas supply tube 506 and port 504 can be divided. Gas supply tube 506 can be divided in whole or in part.

Mask shell 502 can be coupled to cushion 508 for forming a seal around the nose and mouth of a wearer. Arm 540 can extend from mask shell 502 for contacting portions of a wearer's forehead. Arm 540 can be made of more than one piece so as to be adjustable (as shown), or, alternatively, can be one-piece. Arm 540 can have pad 542 on the backside thereof for comfortably abutting against portion of a wearer's forehead. Mask shell 502 and arm 540 can have attachment points 522 for connecting headgear or straps (not shown) to mask 500.

Extending inside from divided port 504, the inside of mask 500 can have separated breathing chambers 524, 526 defined by divider 528. Divider 528 can thus separate the inside of mask 500 into two cavities—nasal breathing chamber 524 and oral breathing chamber 526. Divider 528 can be a one-piece or multi-piece construction. Divider 528 can extend back far enough to be proximate the skin between the base of the nose and the upper lip of a wearer when in use. Divider 528 can be situated around the inner sides of mask shell 502 and cushion 508 so as to form a substantially airtight seal.

Breathable gas can be delivered from nasal breathing chamber 524 to the nostrils of a wearer when in use. Breathable gas can be delivered from oral breathing chamber 526 to the mouth of a wearer when in use. One or more expiration holes 544 can be defined through mask shell 502 for one or both of breathing chambers 524, 526 to allow a user to exhale waste gas from one or both of chambers 524, 526.

Divider 528 can be made of any suitable material and in any suitable shape, as will be readily appreciated by one having ordinary skill in the art. In at least one exemplary embodiment, divider 528 can be made of the same material as cushion 508. For example, divider 528 can be made of an elastomeric material, such as a silicone elastomer. Divider 528 may be uniformly or non-uniformly thick. Divider 528 can be formed integral with cushion 508 and can be suitably mated with the inside of mask shell 502 and port 504.

As another non-limiting example, divider 528 can be made of a rigid plastic, which can also be the same material that mask shell 502 is constructed of. Divider 528 can be integral with mask shell 502 and can be suitably mated with cushion 508. Alternatively, divider 528 can be made to be retrofitably applied to conventional masks.

Still referring to FIGS. 2A and 2B, a flow generator (not shown) can be connected to gas supply tube 506 for delivering breathable gas to mask 500. Gas supply tube 506 can be of any suitable length. For illustrative purposes and in a non-limiting manner, gas supply tube 506 is shown truncated. The flow generator can be a CPAP machine, a BiPAP machine, an IPPV machine, an APAP machine and the like known to one having ordinary skill in the art. Gas supply tube 506 (or portions thereof) can be any flexible, thin-walled tubing known to one having ordinary skill in the art. Other portion or pieces of gas supply tube 506 may be more rigid. For example, gas supply tube 506 may include rigid plastic pieces.

At least a portion of gas supply tube 506 can include gas supply divider 530. Gas supply tube 506 can be fluidly coupled to mask 500. Gas supply divider 530 can split the gas supply tube 506 into nasal channel 532 and oral channel 534 for delivering breathable gas to nasal breathing chamber 524 and oral breathing chamber 526, respectively. Gas supply divider 530 can be planar, or, alternatively, non-planar. In at least one exemplary embodiment, gas supply divider 530 can split gas supply tube into channels 532, 534 of substantially different volumes. Alternatively, gas supply divider 530 can split gas supply tube 506 into channels 532, 534 of substantially equal volume. Accordingly, gas supply divider 530 may be positioned so as to form two unequal cross-sectional areas within gas supply tube 506. Alternatively, gas supply divider 530 may span the diameter of gas supply tube 506 so as to form two substantially equal cross-sectional areas. Gas supply divider 530 may also divide gas supply tube 506 into more than two channels in other embodiments.

Gas supply divider 530 can be constructed of the same material as gas supply tube 106 (or portions thereof). Gas supply divider 530 can be made of a flexible plastic, as one non-limiting example. Gas supply divider 530 can be equally thin-walled as gas supply tube 506 (or portions thereof) or can be thicker and thus more rigid than gas supply tube 506.

Gas supply divider 530 can be integrally formed with gas supply tube 506 (or portions thereof). Alternatively, gas supply divider 530 can be configured for insertion into gas supply tube 506 (or portions thereof). Gas supply divider 530 can be attached within gas supply tube 506 or held within gas supply tube 506 by a mating mechanism. For example, gas supply divider 530 can include a ridge portion of a tongue-in-groove mating system. Lateral groove sections can thus be defined within gas supply tube 506 for receiving the ridge portion.

Still referring to FIGS. 2A and 2B, breathable gas can be communicated through nasal channel 532 and oral channel 534 at different pressures. Moreover, pressurized breathable gas from nasal channel 532 and oral channel 534 can be directed to nasal breathing chamber 524 and oral breathing chamber 526, respectively. Accordingly, the pressurized breathable gas provided to nasal breathing chamber 524 can be under a different pressure than the pressurized breathable gas provided to oral breathing chamber 526.

To provide breathable gas at different pressures to nasal breathing chamber 524 and oral breathing chamber 526, respectively, one or more valves (not shown) or like mechanisms can be situated within or at any divided portion of port 504 or gas supply tube 506. The one or more valves can be set to partially obstruct channels 532, 534 within gas supply tube 506 or at port 504. The one or more valves can be any valve known to one of ordinary skill in the art. Accordingly, one or more valves can regulate the flow of pressurized breathable gas through channels 532, 534. Alternatively, singularly or in conjunction, one or more valves can regulate the flow of pressurized breathable gas entering breathing chambers 524, 526. Valves can have positions ranging from fully opened to fully closed and any selectable position there between. Exemplary valves can be similar to any of valves 236, 238, 336, 338, 436, 438 described above, as will be readily recognized by one having ordinary skill in the art.

In a further exemplary embodiment, mask 500 can include a divided port 504 having at least two openings that may be in fluid communication with at least two gas supply tubes 506. Each of the gas supply tubes 506 may be in fluid communication with a single breathable gas supplying device or each supply tube 506 can be connected to a different gas supplying device. Each of the gas supply tubes 506 can deliver gas at the same pressures or alternatively, the gas supply tubes 506 may also deliver gas at different pressures. Gas supply tubes 506 may each have the same cross-sectional area or they can have different cross-sectional areas. The gas supply tubes 506 may also include valves or other desired pressure or flow regulating mechanisms known to one skilled in the art.

In another exemplary embodiment, each channel 532 and 534 may include at least one divider 530, which can serve to form a plurality of different channels. Each of the plurality of channels 532 and 534 may be in fluid communication with a single breathable gas supplying device or each channel 532 and 534 can be connected to a different gas supplying device. Each of the channels 532 and 534 can deliver gas at the same pressures or alternatively, the channels 532 and 534 may also deliver gas at different pressures. Channels 532 and 534 may each have the same cross-sectional area or they can have different cross-sectional areas. Additionally, channels 532 and 534 may also include valves or other desired pressure or flow regulating mechanisms known to one skilled in the art.

Other mechanisms for controlling gas flow and/or pressure through channels 532, 534 can include providing walls having one or more openings, which may be fixed or adjustable. In other embodiments, walls having different gas permeabilities can be positioned within channels 532, 534. In further embodiments, any other methods or mechanisms for controlling gas flow and/or gas pressure known to those having ordinary skill in the art can be used. For example, nasal channel 532 and oral channel 534 can have different cross-sectional areas, which in itself can be used to regulate gas flow and/or pressure. Additionally, an external approach to changing the cross-sectional areas of channels 532, 534 can be applied, such as various clamps known to one having ordinary skill in the art. Valves and like mechanism for controlling gas flow and/or pressure may be used in combination.

In at least one other exemplary embodiment, a valve feature or like mechanism for providing breathable gas under different pressures to nasal channel 532 and oral channel 534 can be part of a CPAP unit configured to interface with divided gas supply tube 506. In other embodiments, a divided Y connector can be coupled to gas supply tube where each tube extending from an arm of the Y connector leads to a separate CPAP unit for providing breathable gas under pressure to each channel 532, 534.

Separate channels 532, 534 under the control of one or more valves or like mechanisms can allow a doctor to prescribe different pressures or ranges of pressures of breathable gas to be received nasally and orally by a patient.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A ventilation mask comprising:
   a ventilation interface having at least one gas entry port and having a plurality of gas receiving chambers;
   a gas supply tube, wherein the gas supply tube is in fluid communication with the ventilation interface
   wherein the plurality of gas receiving chambers includes a first gas receiving chamber and a second gas receiving chamber and the ventilation mask is structured to allow for a first flow rate into the first gas receiving chamber and a second flow rate into the second gas receiving chamber.

2. The ventilation mask of claim 1, wherein the plurality of gas receiving chambers include a nasal breathing chamber and an oral breathing chamber.

3. The ventilation mask of claim 1, wherein the gas supply tube has a plurality of channels; and
   wherein at least one of the plurality of channels is in fluid communication with at least one of the plurality of gas receiving chambers.

4. The ventilation mask of claim 1, wherein the plurality of gas receiving chambers is configured to receive gas through a single gas entry port during use.

5. The ventilation mask of claim 1, wherein the plurality of gas receiving chambers are not in fluid communication to each other.

6. The ventilation mask of claim 3, wherein at least one of the plurality of channels includes a valve, which adjusts the fluid flow through the channel.

7. The ventilation mask of claim 1, wherein at least one of the plurality of gas receiving chambers includes a valve, which adjusts the fluid flow from the gas supply tube to at least one of the plurality of gas receiving chambers.

8. The ventilation mask of claim 2, wherein the ventilation interface includes a dividing wall that provides a substantially airtight seal between the nasal breathing chamber and the oral breathing chamber.

9. The ventilation system of claim 2, wherein the ventilation mask is adapted to enclose a mouth and a nose of a user.

10. The ventilation mask of claim 1, wherein the ventilation interface includes nasal prongs that are adapted to enter at least one of the nostrils of a user.

11. The ventilation mask of claim 8, wherein the gas entry port abuts the dividing wall.

12. A ventilation mask comprising:
    a plurality of gas receiving chambers, wherein the plurality of gas receiving chambers include a nasal gas receiving chamber and an oral gas receiving chamber;
    wherein the ventilation mask a gas entry port; and
    wherein the gas entry port is in fluid communication with the nasal breathing chamber and the oral breathing chamber;
    wherein the ventilation mask is structured to allow for a first flow rate into the nasal gas receiving chamber and a second flow rate into the oral gas receiving chamber.

13. The ventilation mask of claim 12, wherein the gas entry port is configured to deliver gas to the nasal gas receiving chamber and the oral gas receiving chamber.

14. The ventilation mask of claim 12, wherein at least one of the plurality of gas receiving chambers includes a valve, which adjusts the fluid flow entering the gas receiving chamber.

15. The ventilation mask of claim 12, further comprising:
    a dividing wall that provides a substantially airtight seal between the nasal gas receiving chamber and the oral gas receiving chamber.

16. The ventilation mask of claim 12, wherein the ventilation mask is adapted to enclose a mouth and a nose of a user.

17. The ventilation mask of claim 12, wherein the ventilation mask includes nasal prongs that are adapted to enter at least one of the nostrils of a user.

18. The ventilation mask of claim 15, wherein the gas entry port abuts the dividing wall.

19. A ventilation mask comprising:
    a ventilation interface with a gas receiving nasal chamber and an gas receiving oral chamber;
    a gas supply tube coupled to the ventilation interface for receiving a gas from a flow source;
    wherein the ventilation mask is structured to allow for a first flow rate into the gas receiving nasal chamber and a second flow rate into the gas receiving oral chamber.

* * * * *